United States Patent
March et al.

(10) Patent No.: US 7,910,110 B2
(45) Date of Patent: Mar. 22, 2011

(54) BACTERIOPHAGE-MEDIATED IMMUNISATION AGAINST HEPATITIS

(75) Inventors: John Bernard March, Midlothian (GB); Jason Clark, Edinburgh (GB)

(73) Assignee: BigDNA Limited, Roslin, Midlothian (GB)

( * ) Notice: Subject to any disclaimer, the term of this patent is extended or adjusted under 35 U.S.C. 154(b) by 1535 days.

(21) Appl. No.: 10/529,917

(22) PCT Filed: Oct. 2, 2003

(86) PCT No.: PCT/GB03/04267
§ 371 (c)(1), (2), (4) Date: Oct. 11, 2005

(87) PCT Pub. No.: WO2004/030694
PCT Pub. Date: Apr. 15, 2004

(65) Prior Publication Data
US 2009/0010960 A1 Jan. 8, 2009

Related U.S. Application Data

(63) Continuation-in-part of application No. 10/473,664, filed as application No. PCT/GB02/01413 on Mar. 25, 2002, now Pat. No. 7,128,916.

(30) Foreign Application Priority Data

Oct. 2, 2002 (GB) .................................. 0222824.5

(51) Int. Cl.
*A61K 39/29* (2006.01)
*A61K 39/295* (2006.01)
(52) U.S. Cl. ............... 424/199.1; 424/193.1; 424/194.1; 424/196.11; 424/202.1; 424/204.1; 424/226.1; 424/227.1; 530/806; 530/810
(58) Field of Classification Search .................. None
See application file for complete search history.

(56) References Cited

U.S. PATENT DOCUMENTS

| | | | |
|---|---|---|---|
| 5,736,388 | A | 4/1998 | Chada et al. |
| 6,054,312 | A | 4/2000 | Larocca et al. |
| 7,407,790 | B2 | 8/2008 | Hone |
| 2003/0113293 | A1 | 6/2003 | Bermudes et al. |

FOREIGN PATENT DOCUMENTS

| | | | |
|---|---|---|---|
| EP | 0 181 117 A2 | 5/1986 | |
| WO | WO 96/21007 A2 | 7/1996 | |
| WO | WO 98/05344 | 2/1998 | |
| WO | WO 98/37916 A1 | 9/1998 | |
| WO | WO 98/39031 A1 | 9/1998 | |
| WO | WO 98/56423 A1 | 12/1998 | |
| WO | WO 99/10014 | 3/1999 | |
| WO | WO 99/55720 A1 | 11/1999 | |
| WO | WO 00/67761 A1 | 11/2000 | |
| WO | WO 02/076498 * | 10/2002 | ............... 424/132.1 |

OTHER PUBLICATIONS

Pugh, et al. Expression of the X Gene of Hepatitis B Virus. Journal of Medical Virology. 1986; vol. 20 Issue 3, pp. 229-246.*
Gough, NM. Core and E antigen synthesis in rodent cells transformed with hepatitis B virus DNA is associated with greater than genome length viral messenger RNAs. J Mol Biol. Apr. 25, 1983;165(4):683-99.*
Stoller-Keller, et al. Development of hepatitis C virus vaccines: challenges and progress. Expert Rev Vaccines. Mar. 2009; 8(3):333-45 (abstract only cited).*
Aggarwal and Jameel, Hepatitis E vaccine. Hepatol Int. Sep. 2008; 2(3): 308-315.*
Aujame et al. "Experimental Design Optimization of Filamentous Phage Transfection into Mammalian Cells by Cationic Lipids", *Biotechniques* 28:1202-1213 (2000).
Bastien et al. "protective Immune Responses Induced by the Immunization of Mice with a Recombinant Bacteriophage Displaying a Epitope of the Human Respiratory Syncytial Virus" *Virology* 234: 118-122 (1997).
De Berardinis et al. "Phage Display of Peptide Epitopes from HIV-1 Elicits Strong Cytolytic Response" *Nature Biotechnology* 18:2000.
Gaubin et al. "Processing of Filamentous Bacteriphage Virions in Antigen-Presenting Cells Targets Both HLA Class I and Class II Petptide Loading Compartments" *DNA and Cell Biology* 22(1): 11-18 (2003).
Horst et al. "Gene Transfer to Human Cells: Transducing Phage λplac Gene Expression in $GM_1$-gangliosidosis fibroblasts" *PNAS* 72(9): 3531-3535 (1975).
International Search Report Corresponding to PCT/GB02/01413 mailed Jun. 13, 2003.
Ishiura et al. "Phage Particle-Mediated Gene Transfer to Cultured Mammalian Cells" *Molecular and cellular Biology* 2(6): 607-616 (1982).
Monahan et al. "Viral Vectors for Gene Transfer into Antigen Presenting Cells" *Current Opinion in Molecular Therapeutics* 1(5): 558-564 (1999).
Okayama et al. "Bacteriophage Lambda Vector for Transducing a cDNA Clone Library into Mammalian Cells", *Molecular and Cellular Biology* 5:1136-1142 (1985).
Srivatsan et al. "Plasmid, phage, and genomic DNA-mediated transfer and expression of prokaryotic and eukaryotic genes in cultured human cells", *Cytogenet Cell Genet* 38:227-234 (1984).
Vincent et al. "An In Vitro, Complement-Dependent Model of Particle Transfer from Erythrocytes to Macrophages" *Immunopharmacology* 49(1-2): 90 (2000).
Douglas, R.G. "The Jeremiah Metzger Lecture, Vaccine Prophylaxis Today: Its Science, Application and Politics" *Transactions of the American Clinical and Climatological Association* vol. 109, p. 185-198 (1998).
Ishiura et al. "Stability of the Transformants Obtained by Phage Particle-Mediated Gene Transfer" *Cell Structure and Function* 14:495-499 (1989).
Koide et al. "DNA Vaccines" *Jpn J Pharmacol* 83:167-174 (2000).

* cited by examiner

*Primary Examiner* — Mary E Mosher
*Assistant Examiner* — Stuart W Snyder
(74) *Attorney, Agent, or Firm* — Myers Bigel Sibley & Sajovec, P.A.

(57) ABSTRACT

The present invention relates to vaccines comprising a bacteriophage which has been engineered to express an immunogenic protein/peptide and wherein the surface of the bacteriophage has not been modified to contain proteins/peptides designed to target the phage to receptors on the surface of specific cell types.

17 Claims, 8 Drawing Sheets

BACTERIOPHAGE-MEDIATED IMMUNISATION AGAINST HEPATITIS

RELATED APPLICATIONS

Figure 1:
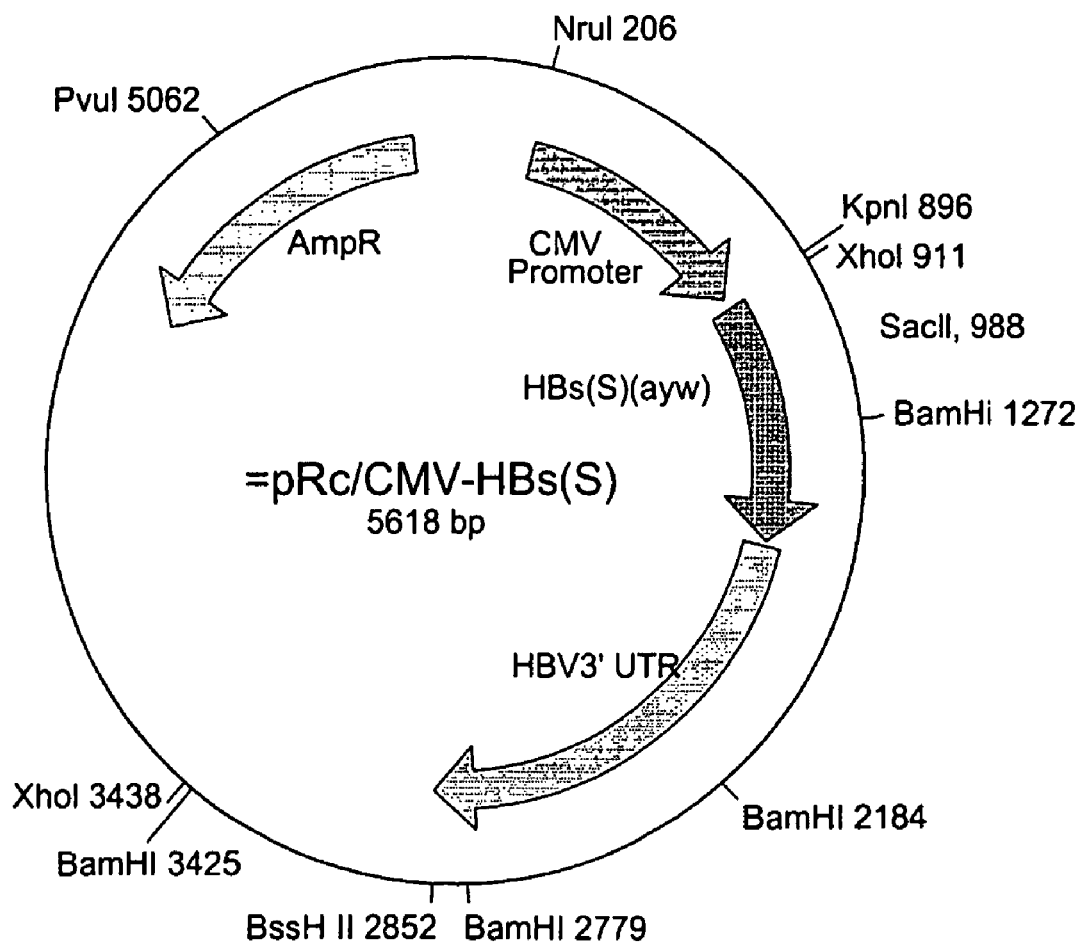
Figure 2A:
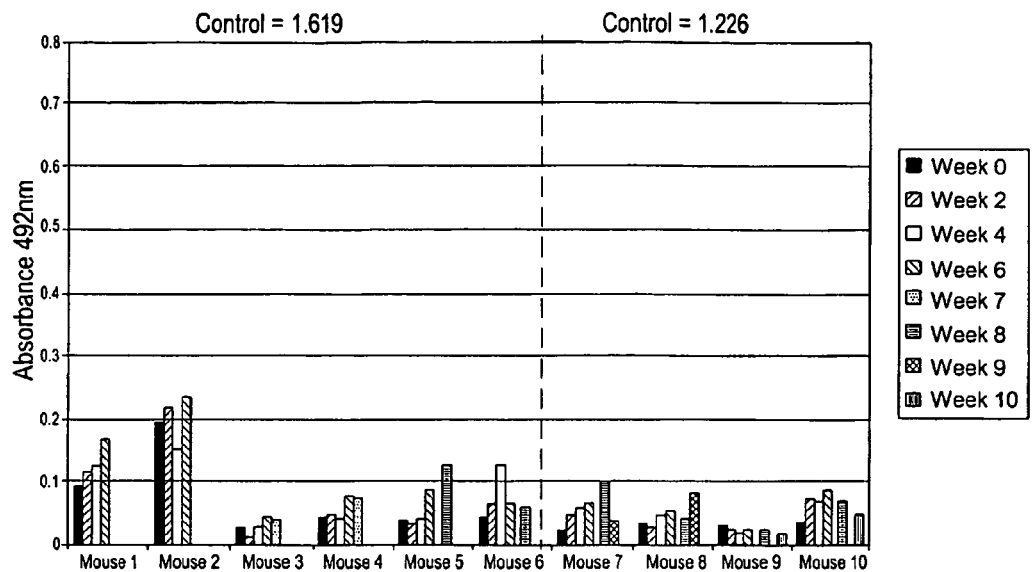
Figure 2B:
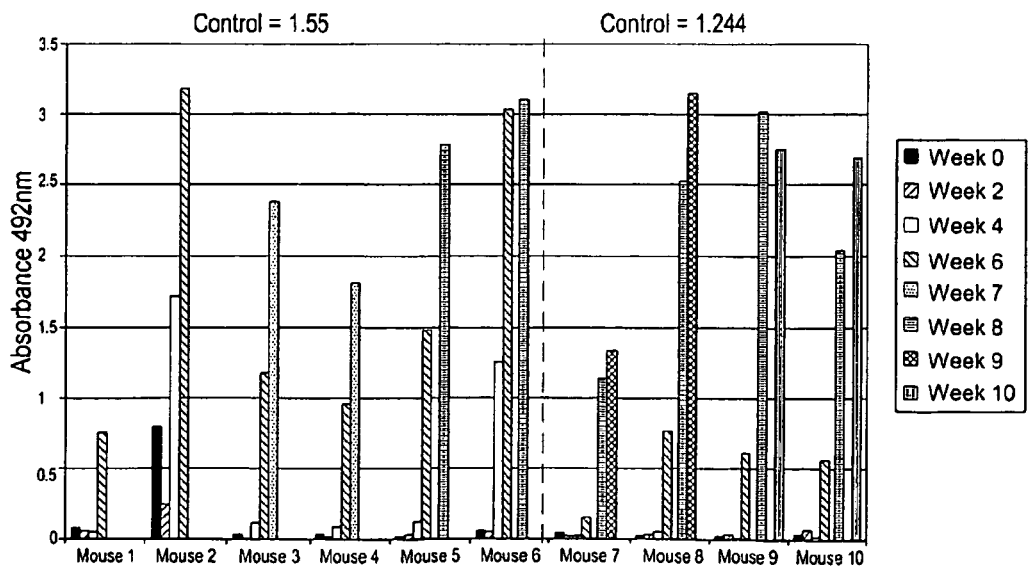
Figure 2C:
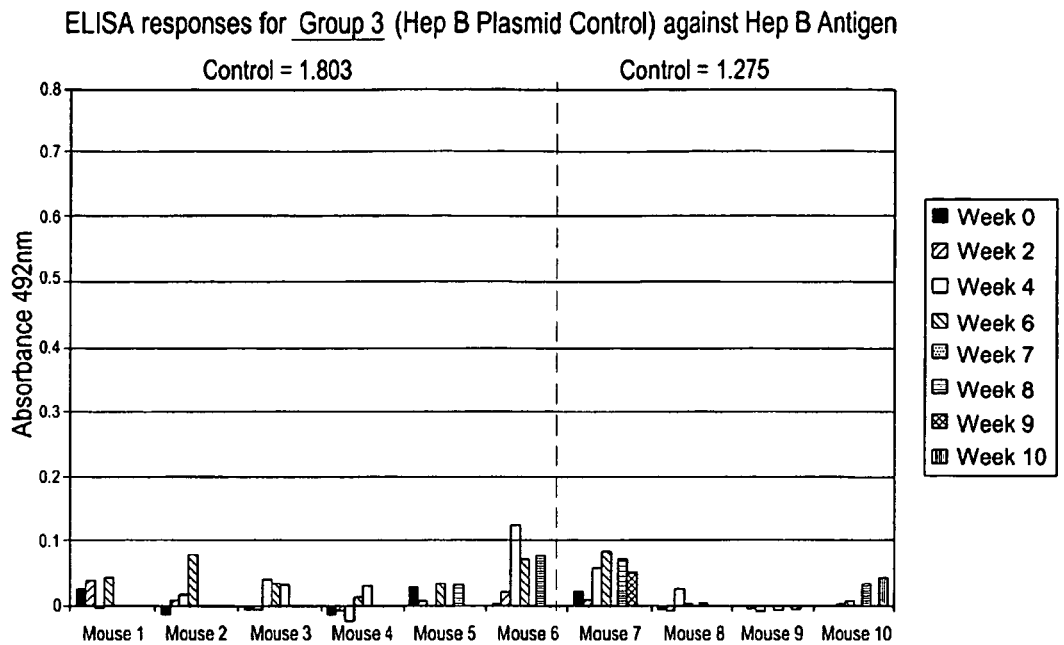
Figure 2D:
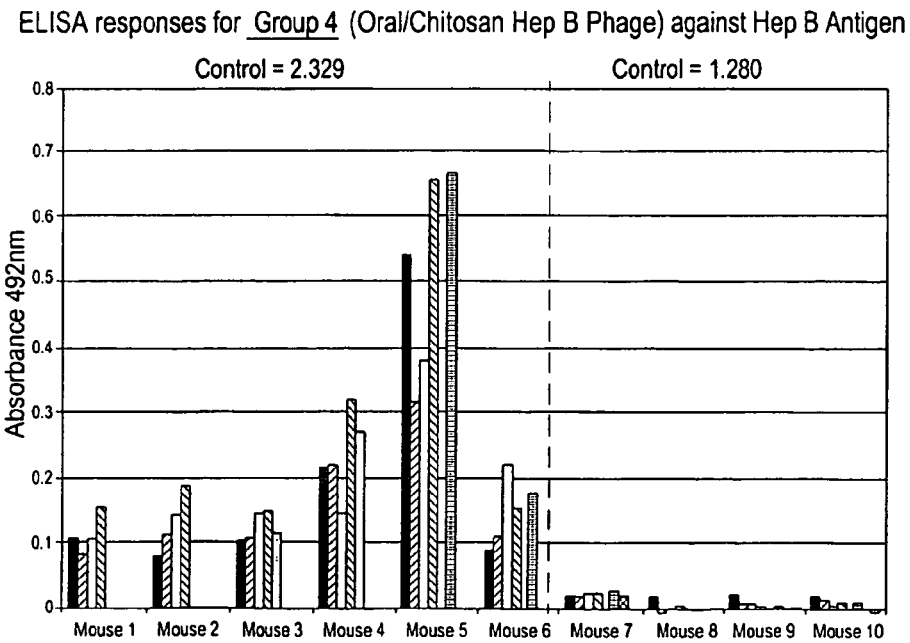
Figure 2E:
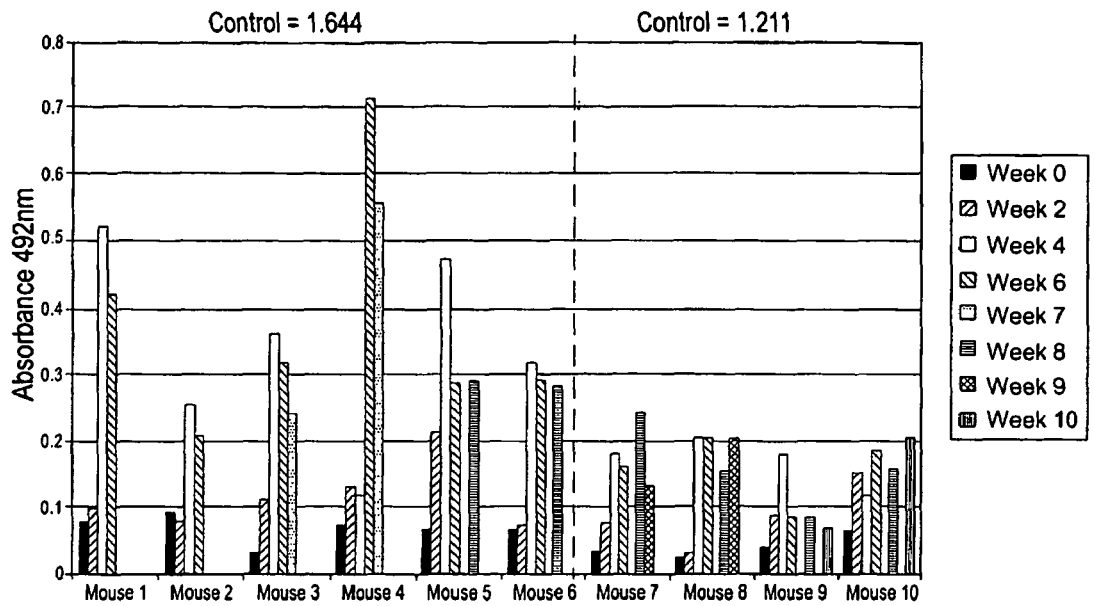
Figure 2F:
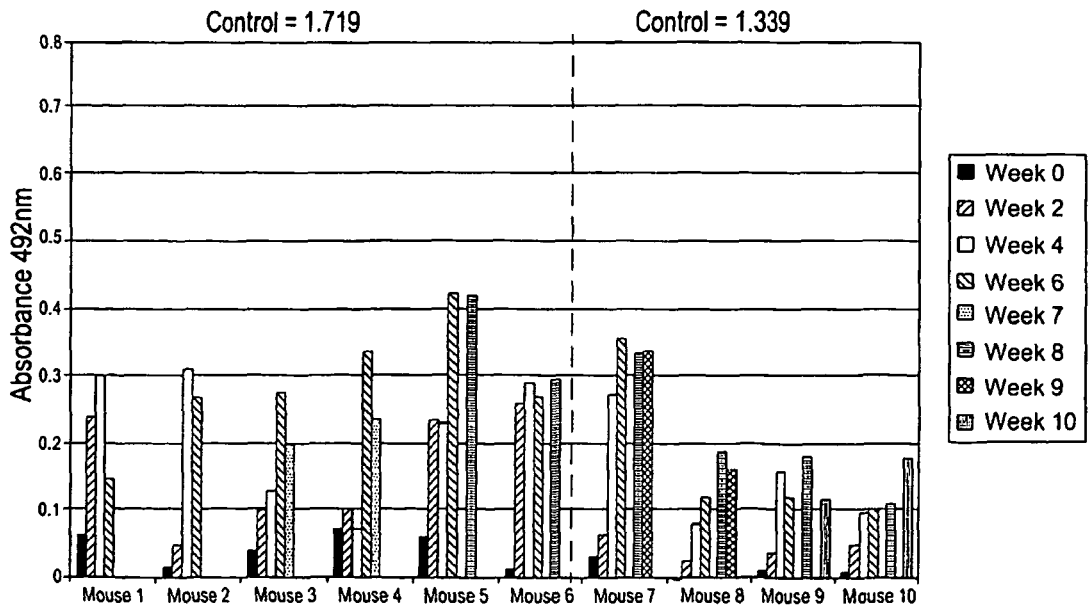
Figure 2G:
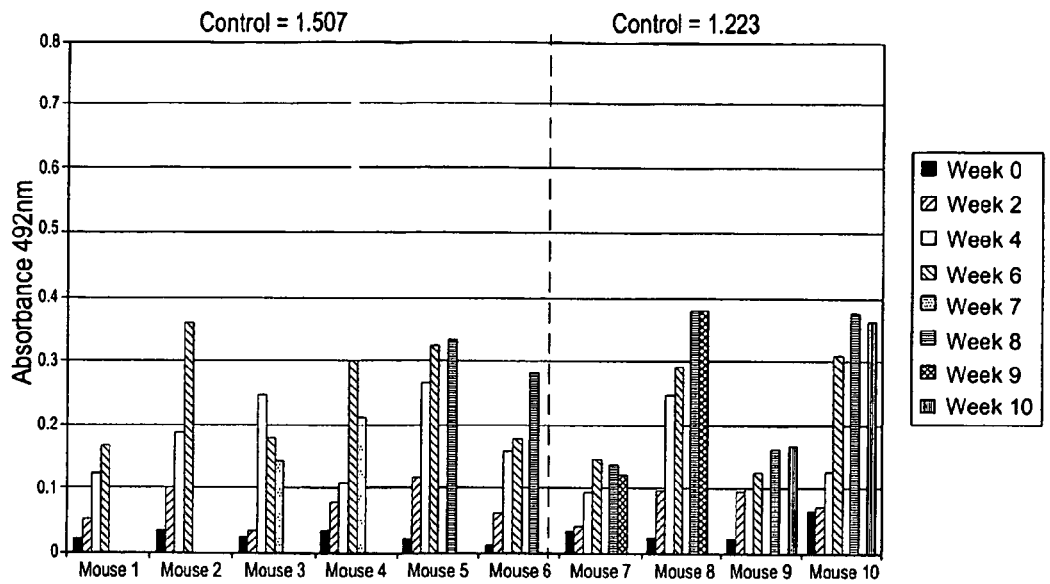
Figure 2H:
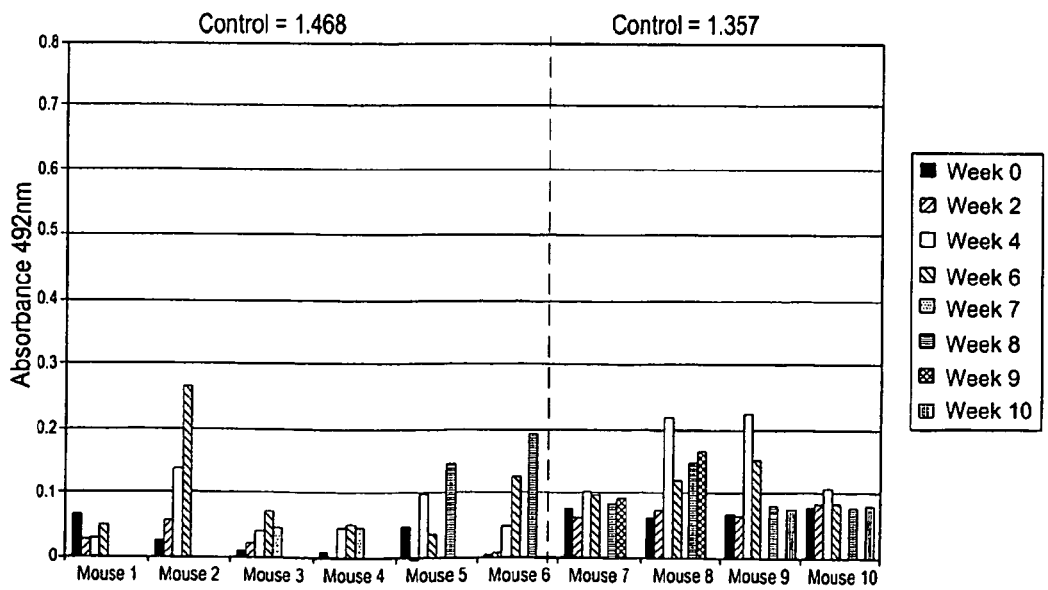

This application is a 35 U.S.C. §371 national phase application of PCT Application No. PCT/GB03/004267, filed in English on Oct. 2, 2003, which claims the benefit of Great Britain Application Serial No. 0222824.5 filed on Oct. 2, 2002, and further it is a continuation-in-part of U.S. patent application Ser. No. 10/473,664, now U.S. Pat. No. 7,128,916, filed Sep. 17, 2003," which is a 35 U.S.C. §371 national phase application of PCT/GB02/01413, the entire contents of each of which are incorporated by reference herein.

The present invention relates to vaccines comprising a bacteriophage engineered to express an immunogenic protein/peptide.

Genetic vaccination is a new and exciting technology in which nucleic acid is used as the vaccine material. (for review see Leitner et al. 2000. Vaccine 18: 765-777). In contrast, traditional vaccines require the use of pathogenic microbes or their antigenic components. There are three classes of "traditional" vaccines: attenuated, killed/subunit, and recombinant. Attenuated vaccines are live microorganisms with reduced pathogenicity and are generally the most effective vaccines. However, they can produce complications if the vaccine agent grows unchecked or reverts to a more pathogenic form. Killed or subunit vaccines require multiple injections, thereby increasing cost and creating logistical problems, and may contain incompletely killed microbes. Recombinant vaccines, in which an antigen from a pathogenic organism is engineered into a non-pathogenic vector can be effective, but difficulties in achieving expression of the antigen in a native conformation often limit efficacy.

To be effective, vaccines need to provide a sufficient dose of antigen for time periods long enough to induce a secondary (memory) response. This poses a problem for traditional vaccines; DNA/RNA vaccines, however, can effectively produce copies of pathogenic antigens for long periods of time, and thus induce both MHC Class I & II responses, as seen with live vaccines. However, for all their promise, DNA vaccines have yet to fulfil their full potential. Despite eliciting a measurable humoral (antibody) immune response, many DNA vaccines exhibit poor efficacy when challenged with the infective organism (Beard, C W & Mason, P W. 1998. Nature Biotech. 16: 1325).

The mechanism by which the nucleic acid enters host cells and induces an immune response is unclear at present. The simplest technique is to administer the DNA as a soluble injection, usually given intramuscularly. Two other techniques in common use are "gene gun" technology, in which DNA is precipitated onto tiny gold particles which are forced into cells with a helium blast, or liposome-mediated transfection, in which DNA is coated with positively charged lipid to form a complex which fuses with the host cell membrane. It is believed that cells surrounding the immunisation site take up the DNA, express the encoded antigen(s), and are recognised as "foreign" by antigen presenting (AP) cells of the immune system, which then proceed to activate T and B cells to elicit an immune response against the antigen.

Limitations would appear to be: (1) Expression is relatively inefficient and non-specific, with the majority of the DNA being expressed in non-AP cells; (2) Expression of foreign antigens in non AP-cells will eventually lead to the death of that cell due to its recognition as being "infected" by the host immune system, thus shortening the potential immune response; and (3) Naked DNA/RNA is highly sensitive to the action of nucleases. It is likely that the majority of nucleic acid used for immunisation is degraded shortly following immunisation.

WO98/05344 describes a method for delivering exogenous genes using a bacteriophage vector wherein the bacteriophage vector has been modified to include on its surface a ligand that binds to a receptor on a target cell. The vectors described are generally intended to be used for gene therapy applications where the vectors are targeted to specific cell types. There is also mention of using the modified bacteriophage vectors to deliver antigenic peptides.

U.S. Pat. No. 5,736,388 describes modified lamboid bacteriophage for delivering nucleic acid molecules to eukaryotic cells in which the bacteriophage has been modified by incorporating mutant tail fibre proteins or by incorporating ligands for eukaryotic cell receptors.

U.S. Pat. No. 6,054,312 relates to filamentous phage particles displaying a ligand on their surface, the ligand being a fusion protein with a phage capsid protein, covalently conjugated to phage particles, or complexed with modified phage particles.

WO99/55720 also describes phage which have been modified to externally display a heterologous targeting protein for use in targeted gene delivery.

However, the aforementioned patents/patent applications all describe modifying the surface of the phage so as allow targeted delivery of nucleic acid to specific cells, generally for gene therapy purposes.

A number of documents (Ishiura, M. et al, Molec. And Cell. Biol., p 607-616, 1982; Aujame, L. et al, Biotechiques, 28 p 1202-1213, 2000; Horst, J. et al, Proc. Natl. Acad. Sci., 72, p 3531-3535, 1975; Jkayama and Dery, Molec. and Cell. Biol. 5, p 1136-1142, 1985; and Srivatsan, E. et al, 38, p 227-234, 1984) relate to the use of phage to transfect cultured mammalian cells and express protein therein. However, there is no suggestion that this could be applied in vivo, or used in the development of vaccines.

It is an object of the present invention to obviate and/or mitigate at least one of the aforementioned disadvantages.

In a first aspect the present invention provides a hepatitis vaccine formulation comprising a bacteriophage particle the surface of which is unmodified and a pharmaceutically acceptable carrier therefor, the bacteriophage particle comprising an exogenous nucleic acid molecule encoding a hepatitis virus polypeptide which is capable of expression and presentation on the surface of an antigen presenting cell of an organism, such that an immune response to said polypeptide is raised in the organism.

Unlike previous disclosures, see for example WO98/05344, U.S. Pat. No. 5,736,388, U.S. Pat. No. 6,054,312 and WO99/55720, it is to be appreciated that the surface bacteriophage of the present invention has not been modified to comprise exogenous peptides/proteins (ie. peptides/proteins not normally present) on the surface of the phage, designed to target the phage to receptors on the surface of specific cell types. It is to be understood therefore that the surface of the bacteriophage may be modified to comprise exogenous peptides/proteins not designed to target the phage to receptors on the surface of specific cell types.

It is understood that the hepatitis vaccine may be used to vaccinate against any hepatitis virus, for example, types A, B, C, D or E, preferably type B. The antigen expressed and presented on the surface of the AP cell may be a surface antigen such as the hepatitis B surface antigen (HBs), although other hepatitis proteins which can elicit an immune response may be expressed.

Moreover, a bacteriophage may be engineered to express more than one hepatitis antigen and may for example express antigens from more than one hepatitis type.

The present inventors have observed that a high dose of bacteriophage particles appears to result in a better immune response being raised. Thus, preferably greater than $10^9$ bacteriophage are administered by dose to the animal, such as greater than $10^{10}$ or $10^{11}$, bacteriophage particles.

Thus, in a second aspect there is provided a vaccine formulation comprising greater than $10^9$ bacteriophage particles, the surface of each particle being unmodified, and a pharmaceutically acceptable carrier therefor, said bacteriophage particles comprising an endogenous nucleic acid molecule encoding a polypeptide which is capable of expression and presentation on the surface of an antigen presenting cell of an organism, such that an immune response to said polypeptide is raised in the organism.

The present inventors have observed that bacteriophage which have not been modified to comprise targeting peptides or ligands on the surface of the bacteriophage particle are taken up by AP cells. Thus, the bacteriophage of the present invention are thought to be recognised as "foreign" and are therefore processed in the normal manner by a host's immune system. Moreover, by modifying the genome of the bacteriophage to include exogenous nucleic acid capable of encoding a foreign peptide/protein, that is a peptide/protein not normally present in a chosen mammalian host, an immune response to this foreign protein is elicited. Thus, the nucleic acid encoding the foreign peptide/protein is expressed (in an antigen presenting cell or otherwise) and presented on the surface of the AP cell. It is to be appreciated that the immune response may be a humoral (ie. antibody) and/or cellular immune response.

Exogenous nucleic acid relates to a non-naturally occurring polynucleotide that is capable of being expressed as an heterologous peptide or protein, that is a peptide or protein which is not normally expressed or is expressed at biologically insignificant levels in a naturally-occurring bacteriophage. The expressed peptide or protein is expressed at a level sufficient to elicit an immune response in a host to which the vaccine has been presented.

It is to be appreciated that according to the second aspect the present invention is applicable to the preparation of a vaccine for practically any infectious disease not necessarily hepatitis, providing that a suitable immuno-protective response can be raised to a protein or proteins of an infectious agent. Examples of suitable diseases include vaccination directly against the disease-causing agent, or alternatively, vaccination against the disease-carrying vector. Such infectious agents or vectors include virus, bacteria, fungi, yeast, protozoa, helminths, insecta, and transmissible spongiform encephalopathies. The present invention would be applicable to infectious diseases of both humans and animals. Lists of suitable diseases are well known to those versed in the art and examples are to be found in the O.I.E. Manual of Standards and Diagnostic Tests 3rd Ed., OIE, Paris 1996, Topley & Wilson's Principles of Bacteriology, Virology and Immunity 8th Ed., Eds. Parker M. T. and Collier L. H., Vol IV (Index), Edward Arnold, London 1990, The Zoonoses: Infections Transmitted from Animals to Man. Bell J. C. et al., Edward Arnold, London 1988 and Parasitology: The Biology of Animal Parasites 6th Ed. Noble E. R. et al., Lea & Febiger, Philadelphia, 1989. In addition the present invention could be used to elicit an immune response against cancer cells by means of the expression of a cancer cell specific antigen as the vaccine protein.

The present invention thus provides a way of encapsulating exogenous nucleic acid eg. DNA inside a stable matrix, in order to protect it from for example nucleases present for example in cells. The "foreign" proteins on the surface of the bacteriophage allow direct uptake of nucleic acid specifically to antigen presenting (AP) cells. Without being bound by theory it is expected the bacteriophage particle is recognised as a foreign antigen. The entire particle is thus taken up directly by the antigen presenting cells of the host immune system, where the protein coat is removed, releasing the DNA which may then move into the nucleus and be expressed. This procedure, is thought to be efficient, since vaccine DNA expression and subsequent polypeptide production should only take place in AP cells; the optimum route for inducing an immune response.

In general the term "polypeptide" refers to a chain or sequence of amino acids displaying an antigenic activity and does not refer to a specific length of the product as such. The polypeptide if required, can be modified in vivo and/or in vitro, for example by glycosylation, amidation, carboxylation, phosphorylation and/or post translational cleavage, thus inter alia, peptides, oligo-peptides, proteins and fusion proteins are encompassed thereby. Naturally the skilled addressee will appreciate that a modified polypeptide should retain physiological function i.e. be capable of eliciting an immune response.

The bacteriophage of the present invention preferably contain appropriate transcription/translation regulators such as promoters, enhancers, terminators and/or the like. Typically the promoter may be a eukaryotic promoter such as CMV, SV40, thymidine kinase, RSV promoter or the like. Conveniently the promoter may be a constitutive promoter. However, controllable promoters known to those of skill in the art may also be used. For example constructs may be designed which comprise the exogenous nucleic acid under control of a constitutive promoter and a controllable promoter. In this manner it may be possible to cause expression of the exogenous nucleic acid initially by way of the constitutive promoter and at a second time point by expression from the controllable promoter. This may result in a stronger immune response.

Many suitable bacteriophage are known to those skilled in the art. An example of a suitable bacteriophage is lambda (λ). Currently, bacteriophage λ is used as a cloning vector during routine DNA manipulation procedures. For these, the DNA is purified away from the phage structure. However, an intact λ phage particle fulfils the criteria listed above; the DNA is contained within a protective protein matrix which is recognised as a foreign antigen by the host immune system. Phage λ normally infects the bacterium *E. coli*, and its DNA is thought to be "inert" in a eukaryotic cell (ie. it will not be expressed). However, if a eukaryotic promoter is incorporated upstream of the vaccine (or foreign) gene of interest, then expression of that gene to provide an antigen ie. protein/peptide should occur if the DNA is taken up by a mammalian cell. Due to extensive use as a routine cloning vector, many variants of λ exist, including some with strong eukaryotic promoters designed to direct expression in mammalian cells. Normally, the relevant section of the λ vector is removed as plasmid DNA prior to further genetic manipulations:— highly purified plasmid DNA from an *E. coli* host will then be used for genetic immunisation. However, if an intact λ phage particle containing a eukaryotic promoter and the vaccine (ie. exogenous) gene of interest is used for immunisation, it is taken up by AP cells. Following protein coat removal, antigen production directly within the AP cell is thought to occur and antigen presented on the surface of the AP cells so as to induce an immune response. In this case only the most basic purification procedure is required to produce phage particles ready for immunisation. An additional advantage of using λ compared to plasmid cloning vectors is that much larger insert sizes can be accommodated.

Other suitable bacteriophage are well known to those of skill in the art and include p1 phage, T phages (eg. T1-T7), Mu, fd or M13, as well as filamentous phage.

Preferred bacteriophage of the present invention have the ability to incorporate exogenous nucleic acid and associated promoters, enhancers, terminators and/or the like of between about 0.5-100 kilobases. For example known lambda phages can accommodate between 9-50 kilobases. In this manner it is possible to express single or multiple copies of a peptide/protein or a plurality of peptides/proteins.

Typically, the bacteriophage of the present invention are abortive to lytic growth in the natural bacterial flora of the chosen mammalian host. Many "laboratory" strains of phage are known for example which are only able to infect non-wild type "laboratory" bacterial strains. Additionally or alternatively the bacteriophage may be abortive to lytic growth of the host bacterial strain in vitro, or require helper phage to grow in vitro. Thus the bacteriophage may contain for example an amber mutation, a temperature sensitive mutation or the like.

Means are generally provided to enhance expression of the exogenous nucleic acid in the AP cells. Such means include methods to help minimise nucleic acid degradation and/or targeting to the nucleus. Examples of such means include the use of chloroquine or other inhibitors of lysosomal/endosomal enzymic catabolism to minimise nucleic acid degradation and/or the use of nuclear localisation signals to direct the nucleic acid to the nucleus.

The vaccine formulation may further comprise a source of the protein which is to be expressed by the bacteriophage. In this manner a host may elicit a primary immune response to the protein and thereafter elicit a further or sustained immune response due to the protein being expressed and presented on the surface of an AP cell.

In a further embodiment the phage could be modified to also express the antigenic protein on the surface of the phage particle. For example it is possible to use intact bacteriophage M13 particles as a vector vehicle. Insert sizes for M13 are considerably smaller than for λ, but the use of "Phage Display" technology (Hawkins, R E et al. 1992, J. Mol. Biol. 226: 889) means that the phage particle can carry a portion of foreign antigen fused to its coat protein. Thus a construct can be made in which the vaccine gene is under control of both a prokaryotic (eg. Lac Z promoter) and a eukaryotic promoter (eg. CMV promoter): when grown in an *E. coli* host, the prokaryotic promoter will direct expression of the vaccine antigen and allow its incorporation into the M13 coat as a protein conjugate, which should elicit a strong primary response following vaccination. Thereafter, following uptake by AP cells, the DNA will be released and the eukaryotic promoter will direct long-lasting expression of the vaccine antigen from within the AP cell, maintaining a strong secondary response.

The exogenous nucleic acid may encode at least a further polypeptide(s), such as a polypeptide capable of augmenting the immune response. The further polypeptide may be an adjuvant protein or polypeptide, such as a cytokine coding, for example, for an interferon such as γ interferon (γIFN), IL-2, IL-6, IL-7, IL-12, CM-CSF and/or other cytokines/chemokines. Moreover, "helper epitopes", such as HepB core antigen may be used to activate B cells and elicit strong T-cell responses. Alternatively or additionally, immunostimulatory signals such as CpG oligodinucleotides may be used.

The bacteriophage may be administered by any suitable route, for example by injection and may be prepared in unit dosage form in for example ampules, or in multidose containers. The bacteriophage may be present in such forms as suspensions, solutions, or emulsions in oily or preferably aqueous vehicles. Alternatively, the bacteriophage may be in lyophilized form for reconstitution, at the time of delivery, with a suitable vehicle, such as sterile pyrogen-free water. In this manner stabilising agents, such as proteins, sugars etc. may be added when lyophilising the phage particles. Both liquid as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% of bacteriophage material.

In a preferred presentation, the vaccine can also comprise an adjuvant. Adjuvants in general comprise substances that boost the immune response of the host in a non-specific manner. A number of different adjuvants are known in the art. Examples of adjuvants may include Freund's Complete adjuvant, Freund's Incomplete adjuvant, liposomes, and niosomes as described, for example, in WO 90/11092, mineral and non-mineral oil-based water-in-oil emulsion adjuvants, cytokines, short immunostimulatory polynucleotide sequences, for example in plasmid DNA containing CpG dinucleotides such as those described by Sato Y. et al. (1996) Science Vol. 273 pp. 352-354; Krieg A. M. (1996) Trends in Microbiol. 4 pp. 73-77.

The bacteriophage may also be associated with a so-called "vehicle". A vehicle is a compound, or substrate to which the bacteriophage can adhere, without being covalently bound thereto. Typical "vehicle" compounds include gold particles, silica particles such as glass and the like. Thus the bacteriophage of the invention may be introduced into an organism using biolistic methods such as the high-velocity bombardment method using coated gold particles as described in the art (Williams R. S. et al. (1991) Proc. Natl. Acad. Sci. USA 88 pp. 2726-2730; Fynan E. F. et al. (1993) Proc. Natl. Acad. Sci. USA Vol. 90 pp. 11478-11482).

In addition, the vaccine may comprise one or more suitable surface-active compounds or emulsifiers, eg. Span or Tween.

The mode of administration of the vaccine of the invention may be by any suitable route which delivers an immunoprotective amount of the virus of the invention to the subject. However, the vaccine is preferably administered parenterally via the intramuscular or deep subcutaneous routes. Other modes of administration may also be employed, where desired, such as via mucosal routes (eg. rectal, oral, nasal or vaginal administration) or via other parenteral routes, ie., intradermally, intranasally, or intravenously. Formulations for nasal administration may be developed and may comprise for example chitosan as an adjuvant (Nat. Medicine 5(4) 387-92, 1999).

It will be understood, however, that the specific dose level for any particular recipient organism will depend upon a variety of factors including age, general health, and sex; the time of administration; the route of administration; synergistic effects with any other drugs being administered; and the degree of protection being sought. of course, the administration can be repeated at suitable intervals if necessary.

In a further aspect therefore, the present invention provides a method of immunising, prophylactically and/or therapeutically, a human or animal, comprising administering to the human and/or animal an effective dose of a vaccine formulation as described herein. It being understood that an effective dose is one which is capable of eliciting an immune response in the human and/or animal.

In a further aspect there is provided use of a bacteriophage particle comprising an exogenous nucleic acid molecule encoding a polypeptide which is capable of expression and presentation on the surface of an antigen presenting cell of an organism, such that an immune response to said polypeptide is raised in the organism for the manufacture of a vaccine for vaccinating against a particular disease.

Preferably the disease to be vaccinated against is hepatitis, for example hepatitis B.

Preferably the medicament per unit dose comprises greater than $10^{10}$ bacteriophage particles, such as greater than $10^{10}$ or $10^{11}$.

The present invention will now be described further by way of example and with reference to the Figures.

A BRIEF DESCRIPTION OF THE FIGURES

Figure 3:
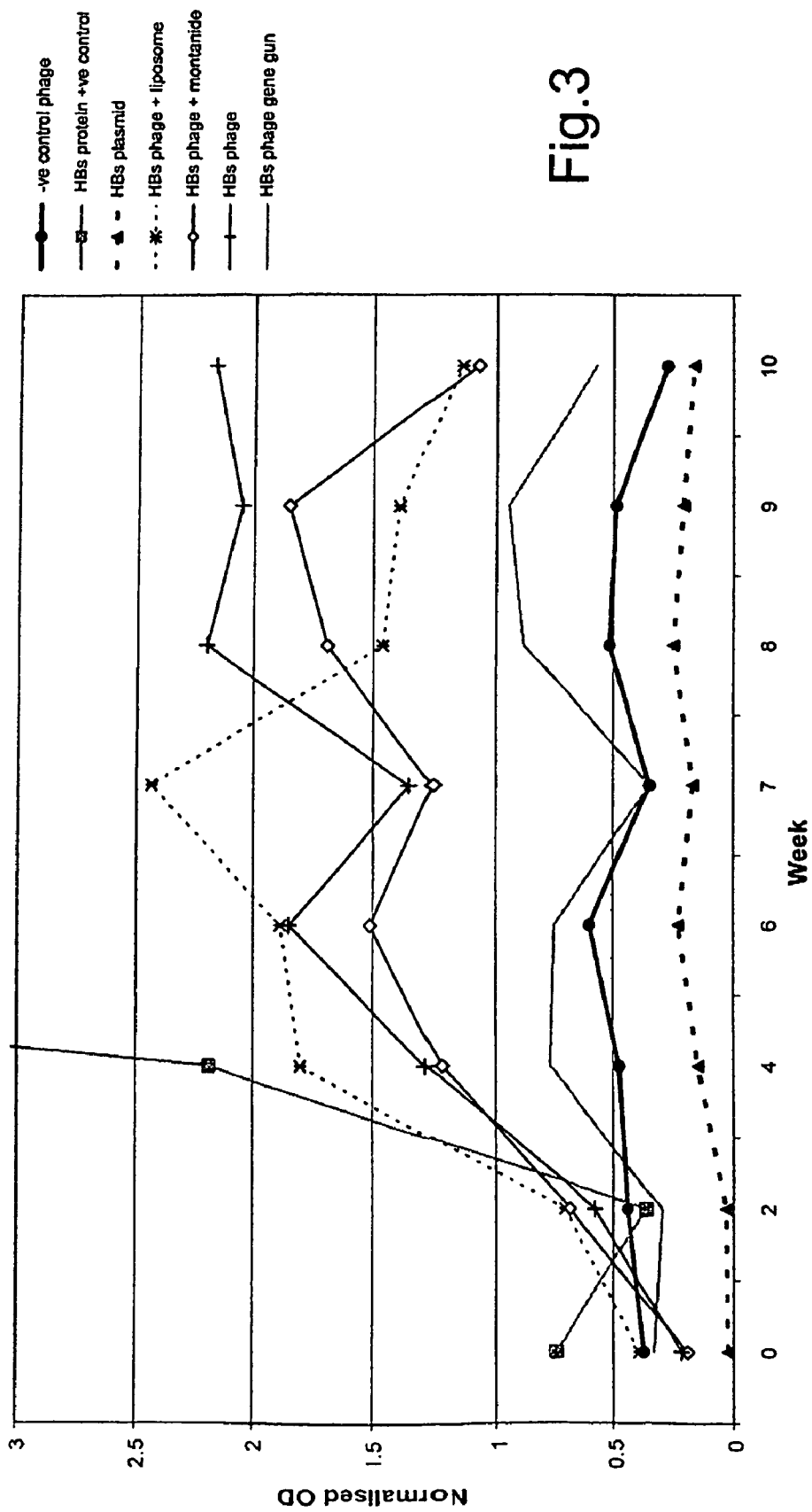
Figure 4:
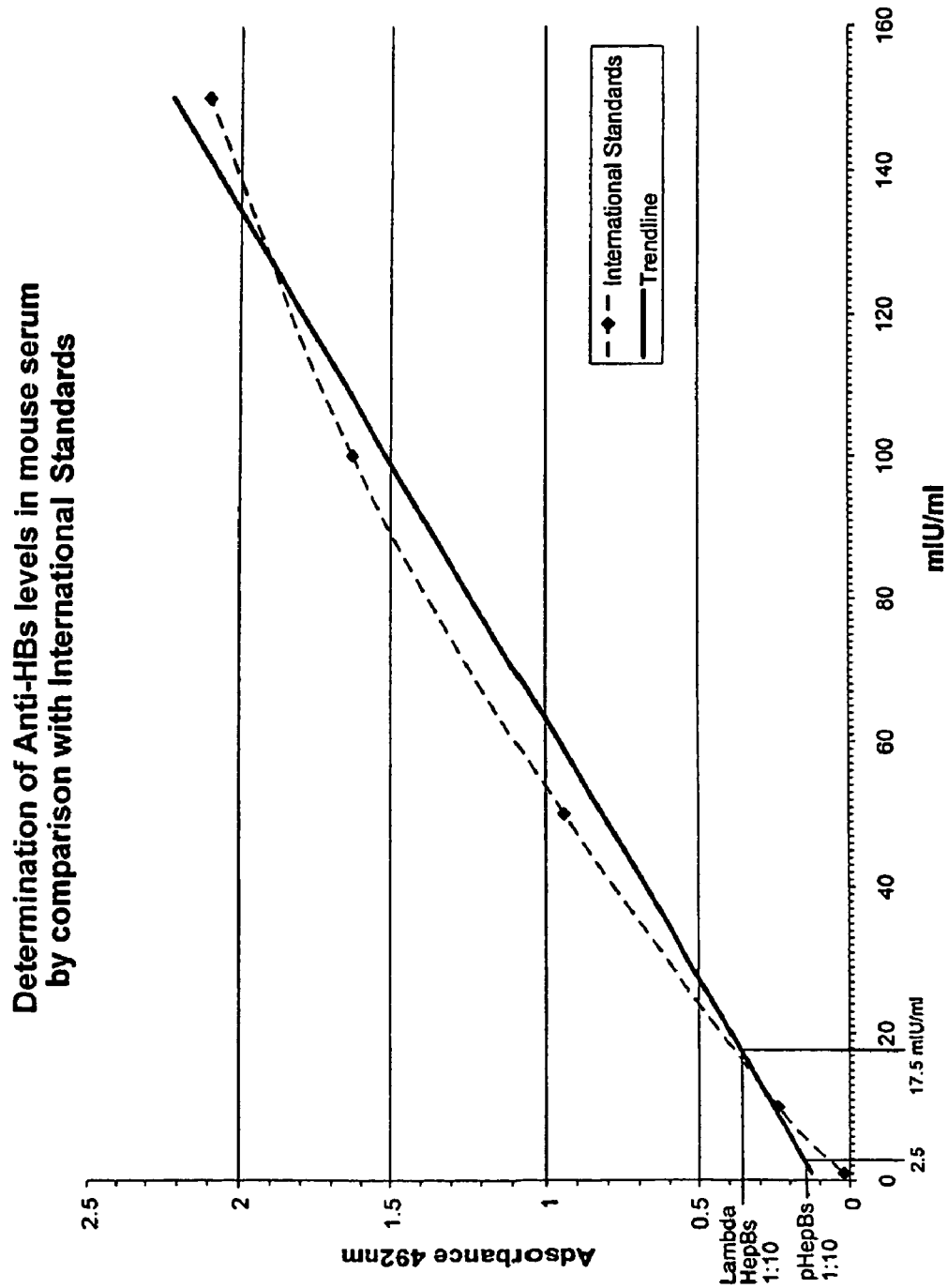
Figure 5:
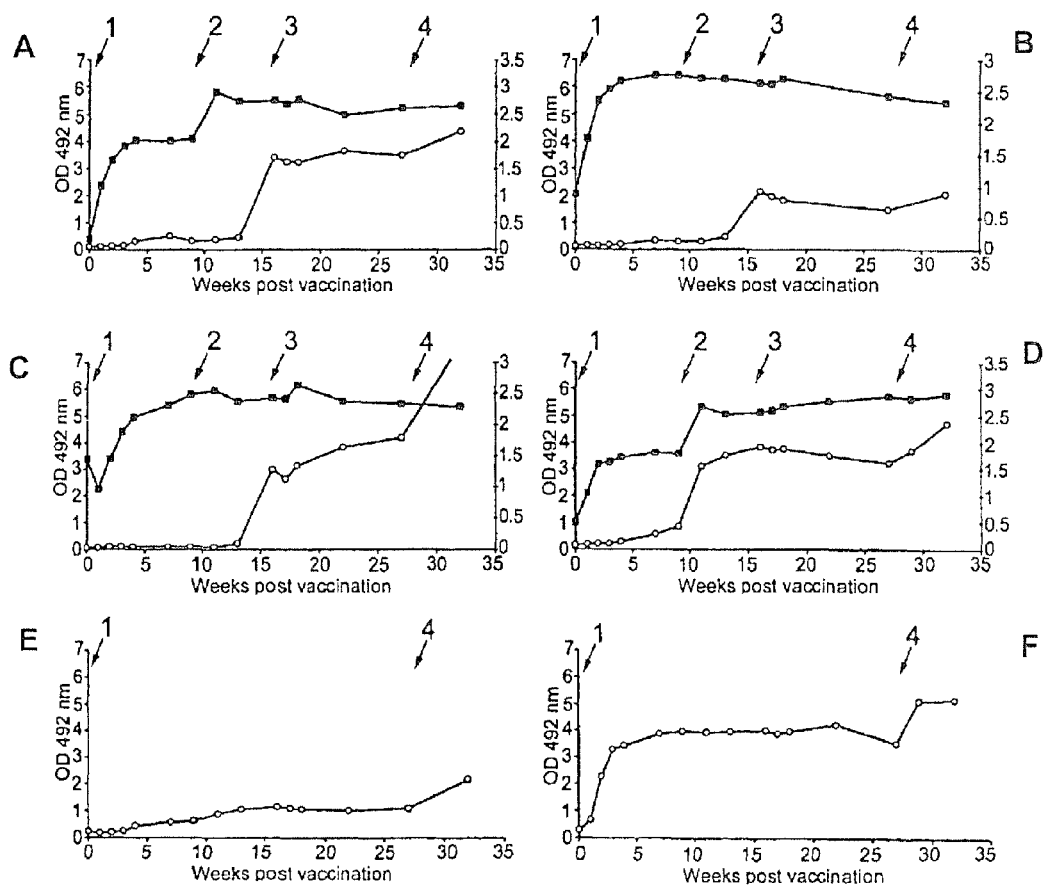

FIG. 1 shows a schematic diagram of the pRc/CMV-HBs(S) vector used to generate a engineered lambda phage according to the present invention;

FIGS. 2(a)-2(h) shows time course graphs showing ELISA responses of various hepatitis constructs administered to mice. Eight groups of mice were used and the samples from each group placed on two separate ELISA plates (see Example). The dashed vertical line distinguishes between the two ELISA plates with samples from Groups 1-6 on one ELISA plate and samples from Groups 7-10 on the other plate. As noted at the top of the graphs, a separate control was used for each ELISA plate;

FIG. 3 shows a graph depicting the group averages of the data shown in FIG. 2;

FIG. 4 shows a graph of the determination of Anti-HBs levels in mouse serum by comparison with International Standards; and FIG. 5 shows antibody responses against HBsAg (open circles, left hand scale) and whole bacteriophage (closed squares, right hand scale) in rabbits vaccinated with λ-HBsAg (A-D) and recombinant HBsAg (E+F), as measured by ELISA. Rabbits A-D were vaccinated (shown by arrows) with λ-HBsAg at weeks 0, 9, 15 and 27. Rabbits E and F were vaccinated with recombinant HBsAg at weeks 0 and 27. For HBsAg plates a monoclonal antibody (clone NF5, Aldevron) was used at a dilution of 1:50,000, while a mouse polyclonal antiserum (1:500) was used for the phage-coated plates. The signal from each serum sample was normalised to the signal from this standard to allow the relative signal to be compared between different plates.

EXAMPLE

Bacteriophage-Mediated Immunisation Against Hepatitis B

Preparation of Hepbs Bacteriophage Vector—λHepbs
Cloning of Hep B Expression Cassette into Lambda Phage.

The plasmid pRc/CMV-HBs(S) (pCMV-S) (Aldevron) (see FIG. 1) was cloned into the EcoRI site of λ-gt11 (Stratagene). Although there is no EcoRI site in the pCMV-S vector there is an MfeI site which gives compatible sticky ends. The MfeI site is at base 160 on the plasmid, whereas the start of the Cytomegalovirus eukaryotic promoter is at base 206, so a single cut with this enzyme does not interfere with the expression cassette.

Plasmid (16 ml at 1 µg/µl) DNA was digested with 20 units of MfeI (New England Biolabs) in the manufacturers recommended buffer for 2 hours at 37° C. Successful digestion was confirmed by running 1 ml of digest on a 1% agarose gel.

Digested plasmid DNA was then treated by phenol/chloroform extraction and ethanol precipitation. The digest was made up to a final volume of 200 µl with distilled water. An equal volume of phenol:chloroform:isoamyl alcohol (35:34:1) (Fisher Biosciences UN2821) was added mixed and spun at 13 000 rpm in a microfuge in phase lock tubes (Eppendorf 0032 007.953). The upper aqueous phase was then removed and extracted with a equal volume of chloroform in the same tube.

After extraction, the aqueous phase was transferred to a fresh tube and 22 µl of 3M sodium acetate was added to give a final concentration of 0.3M. Two volumes of ice cold ethanol was added, the tubes mixed and stored at −20° C. overnight. Tubes were then spun at 13 000 rpm, the supernatant decanted and 750 µl of ice cold 70% ethanol added. The tube was centrifuged at 13 000 rpm for 2 mins. The supernatant was removed and tubes were left to stand in an inverted position for 10-15 mins to remove all traces of alcohol. The pellet was then resuspended in 15 µl of sterile distilled water.

The extracted DNA was checked for purity concentration by running 1 µl on a 1% agarose gel and by checking the OD 260/280 ratio.

Ligations were then performed using this purified DNA and EcoRI digested calf intestinal alkaline phosphatase treated λ-gt11 from Stratagene (Cat number 234211). 2 µl of lambda DNA (0.5 µg/µl) was added to 1.5 µl of digested plasmid which had been diluted to 90 ng/µl. gt11 is approx. 43 kb and the insert approx. 5.6 kb, so using 1 µg gt11 and 135 ng insert gives a 1:1 molar ratio. 3U of DNA ligase (Promega M1801) and appropriate buffer was added and the volume made up to 10 µl with distilled water. A control ligation was also used which was set up as described but 1.5 µl of water was added instead of insert DNA. Ligations were incubated at 4° C. overnight.

After ligation, 1 µl of the ligation mix was run on an agarose gel, alongside unligated lambda DNA to confirm that the insert was in place. The insert could not be excised by EcoRI or MfeI digestion as neither site would be present after ligation, so the overall size difference was used as confirmation.

The ligated DNA was in vitro packaged using the Promega lambda packagene system (cat. K3154). 5 µl of ligation and control reactions as described above were added to 25 µl of packagene extract. A third reaction was also set up using the positive control DNA supplied with the packagene kit. All reactions were left to incubate for 3 h at room temperature. After incubation 225 µl of phage buffer (see packagene instructions) was added to stop the reactions and 12.5 µl of chloroform added. Tubes were mixed well and the white precipitate allowed to settle. The clear supernate contained the packaged phage.

Packaged phage were titrated using the protocols described in the packagene manual. Briefly, serial dilutions of phage were made (1:1000, 1:10 000) in phage buffer and 100 µl each dilution added to 100 µl *E. coli* LE392 in exponential growth phase (to produce LE 392 in exponential phase sub a fresh overnight grown at 37° C. 1:100 into fresh pre-warmed medium and grow with shaking at 37° C. for 2.5 h). Cells and phage were well mixed and incubated at 37° C. for 30 mins. 3 mls TB top agar (1 g bacto-tryptose, 0.5 g NaCl, 0.8 g agar in 100 mls $H_2O$— autoclave, cool to 60° C. and add 1 ml of 1 M $MgSO_4$) at 48° C. was then added to the cells/phage, mixed well and then poured onto LB-agar plates which had been pre-warmed to 37° C.

After overnight incubation plaques were counted. Plates of phage packaged from ligations with the insert had counts which were 150-200 times higher than the no insert controls. Calculated packaging efficiency was $4.2\times10^6$ recombinants/ μg DNA.

6 positive and 2 negative clones were picked and small scale phage amplifications performed by standard methods (Sambrook, et al. 1989, Molecular cloning: a laboratory manual. Cold Spring Harbour Laboratory Press, N. Y.). Samples of these 8 phage picks were subsequently plated as described above on E. coli XL1-blue cells in the presence of X-gal and IPTG. Inserts in the EcoRI site of gt11 disrupt the lacZ gene, so blue/white colour selection was used to confirm the presence of inserts in the clones. Phage with inserts gave white plaques, whereas phage without inserts gave blue plaques. 5 of the 6 phage picked from the plates with inserts gave blue plaques and on of these was picked for subsequent work.

To definitively confirm the presence of the insert, genomic DNA was extracted from the selected phage clone using a Promega Wizard lambda DNA extraction kit (cat A7290). PCR was then performed using primers specific for the pCMV-s plasmid. Other primers situated on either side of the EcoRI cloning site of λ-gt11 were used to sequence across the cloning site, further confirming that the insert was present.

Standard large scale liquid cultures at low multiplicity (Sambrook et al., 1989, Molecular cloning: a laboratory manual. Cold Spring Harbour Laboratory Press, N. Y.) were then used to produce bulk quantities of the phage (λHepBs) for use in subsequent DNA vaccination trials.

Vaccination Protocol

Eight groups of mice, each containing 10 mice were tested. Mice groups were as follows: —
(1) Negative control. Immunised intramuscularly (i.m.) with a non-expressing bacteriophage (λ $cI^{857}$)
(2) Positive control. Immunised with recombinant Hepatitis B surface antigen (HBsAg).
(3) 'Naked' DNA vaccination positive control. Immunised with plasmid expressing the HepB surface antigen under the control of cytomegalovirus promoter (pRC/CMV-HBs [S])
(4) Bacteriophage λ expressing the HepB surface antigen under the control of cytomegalovirus promoter (λHepBs). Oral/nasal administration, bacteriophage given as a complex with the mucosal adjuvant chitosan.
(5) λHepBs, i.m. injection, complexed with liposomes.
(6) λHepBs, i.m. injection, administered in oil-based adjuvant (Montanide 206).
(7) λHepBs, i.m. injection, no adjuvant, in SM buffer only.
(8) λHepBs, intradermal/subcutaneous immunisation using a Bio-Rad Helios compressed nitrogen gas 'gene gun' to fire vacuum-desiccated bacteriophage particles through the skin.

Preparation of Vaccines and Immunisation Protocols: Mice were bled every two weeks. Mice were vaccinated at week 0 and week 3. Prior to vaccination, mice were anaesthetised using inhaled halothane (except for Group 8).

Vaccination Procedures:—

Groups 1-3 and 5-7 (intramuscular immunization). The hindlimbs were shaved to allow better access to the tibialis anterior muscle. A 27G×¾ inch was used to inject samples through the skin. The tip of the needle was about 3 mm lateral to the anterior tibial tuberosity. The needle tip was inserted 3 mm and samples (plasmid DNA, phage, or recombinant HepB surface antigen [HBsAg]) was injected slowly, over about 10 seconds. The needle was held in place for another 5-10 seconds, then slowly removed.

Vaccine Preparation:—

Group 3: Plasmid DNA was presented in endotoxin free phosphate buffered saline (PBS) at a concentration of 0.5 mg/ml and 50 μl was be used per mouse (25 μg DNA per mouse).

Group 2: Mice were injected with 1 μg of recombinant HBsAg in 50 μl endotoxin free PBS.

Groups 1 and 7: Bacteriophage were given in SM buffer (per litre; NaCl 5.8 g, $MgSO_4/7H_2O$ 2 g, 1 m Tris.HCl (pH 7.5), 50 ml, 2% gelatin solution 5 ml) at a concentration of $1\times10^{13}$/plaque forming units (pfu) per ml. 50 μl of phage were injected, equivalent to a dose of $5\times10^{11}$ phage per mouse.

Group 5: Per mouse; $2\times10^{11}$ phage (equivalent to 5 μg DNA) were given coated with transfectam (Promega) cationic lipid. Preparation: 20 μl of phage (in SM buffer) were added to 20 μl of 150 mM NaCl. 10 μg of transfectam in a volume of 10 ml was added and the solution was mixed and left for 10 min to 3 h before injecting intramuscularly as described. Injection volume, 50 μl per mouse.

Group 6: 25 μl of phage in SM buffer at a concentration of $2\times10^{13}$/ml was mixed with an equal volume of Montanide 206 oil adjuvant (Seppic, Paris, France), and each mouse was immunised intramuscularly with 50 μl of vaccine ($5\times10^{11}$ phage per mouse).

Group 4 (oral/nasal immunization): 10 μl of 1% chitosan ([Fluka, medium molecular weight], 10 mg per ml in 1% acetic acid) was added dropwise to $1\times10^{13}$ phage in 100 μl of SM buffer to make a stock preparation. Prior to administration the suspension was briefly vortexed. When mice were just beginning to come round from anaesthetic, a 5 μl drop was administered to each nostril using a Gilson-type pipette.

Group 8 (Gene Gun): A Bio-Rad Helios gene gun was used to deliver phage particles. $10^{11}$ phage particles in 10 μl of SM buffer were transferred to the Gene-Gun plastic tube cartridges, frozen at −70° C., then freeze dried overnight. The abdomen of each mouse was shaved and a single shot was administered per mouse per immunization at a pressure of 500 psi.

| Bleeding schedule:— 10 Mice per group, |
|---|
| Mice 1-2, bled weeks 0, 2, 4, 6 |
| Mice 3-4, bled weeks 0, 2, 4, 6, 7 |
| Mice 5-6, bled weeks 0, 2, 4, 6, 8 |
| Mice 7-8, bled weeks 0, 2, 4, 6, 8, 9 |
| Mice 8-9, bled weeks 0, 2, 4, 6, 8, 10 |

Therefore not all mice were bled at each time point, and this explains the gaps in some mouse bleeds in FIG. 2.

Results

Antibody response to HBsAg measured by ELISA.

Time course antibody responses were measured for each individual mouse within each group. A 1:50,000 dilution of an anti-HBsAg monoclonal antibody was included on each individual ELISA plate to allow for standardization between different plates (result shown as 'Control' value on the relevant section of each graph). Results are shown in FIG. 2 (groups 1 to 8). FIG. 3 shows the group averages of the data presented in FIG. 2.

Significant antibody responses were observed in groups 2 (recombinant HepBs) and groups 5-7 (HepBs with liposomes, montanide and no adjuvant respectively). Much lower, or non-existent responses were observed in the other groups. (The apparent increase in group 4 was a non-specific edge effect of the ELISA plate which affected all bleeds, this is being repeated).

To quantify the anti-HepB surface antigen response in mice, final bleeds were compared to international standards (Bio-Rad Monolisa anti HBs standards catalogue number 72399). 1:10 dilutions of mouse serum were examined by indirect ELISA. Plates were coated with 100 μl/well of HBs at 1 μg/ml (giving 100 ng per well) in 0.2 M sodium carbonate coating buffer at pH 9.6. Plates were left to coat overnight at room temperature.

After overnight incubation the plates were rinsed once with PBS-Tween and 200 μl per well 5% Marvel skimmed milk powder in PBS-Tween added and left for 30 mins at room temperature to block unbound sites.

Block solution was then poured off and 100 μl of 1:10 dilutions of mouse primary antiserum in blocking buffer were added, with block solution alone used as a no primary control. Standards were used as provided, with 100 μl being added per well. The exception was that a 1 mIU/ml (milli-international units/ml) standard was prepared by diluting the 10 mIU/ml standard 1:10 in PBS. Plates were then incubated at room temperature for 2.5 hours.

After incubation, primary serum samples were removed and the plates were washed 5 times with PBS-Tween. Secondary antiserum was than added. A 1:500 dilution of horse radish peroxidase labelled anti-human IgG antibody (Sigma catalogue number A-8667) was used, with 100 μl being added per well. Anti-human serum was used as the secondary antibody, since the 'International Standards' provided were human IgG. Although the samples to be tested were mouse serum, it was expected that there would be sufficient cross reactivity between mouse and human immunoglobulin for the HRP-labelled secondary antibody to detect both, although the figures obtained with the mouse serum were likely to be lower than the actual values. Plates were incubated with secondary antibody for 1.5 hours at room temperature.

Plates were then washed 5 times with PBS-Tween and developed by adding 200 μl/well of Sigma Fast OPD development solution (catalogue number P9187) per well. Plates were developed for 15 mins and then stopped by the addition of 50 μl/well 3M sulphuric acid. Plates were read in an automatic plate reader at 492 nm.

Selected results are shown in FIG. 4.

1:10 dilutions of serum from a mouse immunised with λNHepBs in liposomes (Group 5, Mouse 4) gave a response equivalent to 17.5 mIU/ml, whereas a mouse immunised with the control pRC/CMV-HBs[S]) (Group 3, Mouse 3) gave a response equivalent to 2.5 mIU/ml. The recognised international level for protection is 10 mIU/ml of serum, indicating that immunisation with λHepBs resulted in antibody titres (at a 1:10 dilution) greater than the international levels recognised for protection. Further examples were; Gp 6 (λHepBs plus Montanide) Mouse 5, 16 mIU/ml @ 1:10 dilution and Gp 7 (λHepBs only) Mouse 8, 14 mIU/ml @ 1:10 dilution. It is to be expected that the antibody levels would be higher when tested using undiluted mouse serum. It should also be recognised that since anti-human secondary antibody was used against primary mouse serum in the test samples (rather than a specific anti-mouse HRP conjugate), these results are probably an under-representation of the actual antibody titres.

Example 2

Further Experiments Relating to Bacteriophage-Mediated Immunisation Against Hepatitis B Immunisation of Rabbits Rabbits were vaccinated with 200 μl λ-HBsAg given intramuscularly in saline buffer at a concentration of $2\times10^{11}$ phage per ml ($4\times10^{10}$ phage, 2 μg DNA per rabbit). Phage vaccines were given at weeks 0, 9, 15 and 27. Rabbits treated with recombinant hepatitis B surface antigen (HBsAg-Aldevron) were given protein intramuscularly in 200 μl saline buffer at a concentration of 25 μg/ml (5 μg protein per rabbit) at weeks 0 and 27. Rabbits were bled regularly and antibody responses quantified by ELISA.

ELISA Measurement of Antibody Responses

Antibody responses against recombinant HBsAg or bacteriophage λ coat proteins were measured by indirect ELISA. ELISA plates were coated overnight in 0.05M sodium carbonate buffer at pH 9.2 with either 100 ng of purified HBsAg (Aldevron) or $10^9$ bacteriophage (50 ng) per well. Coating buffer was then removed and 200 μl/well blocking buffer (5% Marvel dry skimmed milk in PBS-Tween) was added for 30 min at 37° C. Blocking buffer was then removed and primary antibody was added at a dilution of 1:50 in blocking buffer at 100 μl/well and plates were incubated overnight at 4° C. Plates were then washed 5 times in PBS-Tween and anti-rabbit horse radish peroxidase-labelled secondary antibody (DAKO) added for 1 hour at 37° C. at the manufacturer's recommended dilution. Plates were then washed 5 times in PBS-Tween and 200 μl/well substrate (SIGMA Fast-OPD tablets) added and the plates developed for five (phage plates) to thirty (HBsAg plates) minutes in the dark. The reaction was stopped by the addition of 50 μl/well of 3M $H_2SO_4$ and the optical density read at 492 nm. End-point titrations were performed by adding 100 μl of diluted primary antibody (1:10-1:50 dependent upon estimated titre) in blocking buffer to the first well on an ELISA plate and serially diluting 1:1 across all 12 columns of the plate. A cut-off value of $OD_{492NM}=0.2$ was used to calculate the end point titre for each serum sample.

Results

To look at immune responses in animals other than mice and to determine whether additional vaccinations would give more consistent responses, four rabbits were immunised with the λ-HBsAg reporter construct and two with recombinant HBsAg protein. Greater intervals were left between the injections and four (λ-HBsAg) or two (recombinant HBsAg) were given in total, compared to two in earlier experiments, with bleeds being taken every 1-3 weeks. Antibody titres were measured by ELISA against recombinant HBsAg (FIG. 5). Following two λ-HBsAg vaccinations, inconsistent responses were again seen against the phage-encoded HBsAg vaccine antigen. One out of four rabbits treated with λ-HBsAg showed a significant response against HBsAg (FIG. 5D), whereas the remaining three animals showed low level gradual increases. These ratios were similar to those observed in mice following two vaccinations with λ-EGFP (i.e. 25% of animals exhibiting a response to EGFP following two vaccinations with reporter phage vaccine). After three vaccinations however, all rabbits showed significantly increased anti-HBsAg responses, comparable to, or in excess of those produced by a single vaccination with recombinant HBsAg protein (FIG. 5). A fourth vaccination with λ-HBsAg resulted in a marked increase in anti-HBsAg titre in a single animal (FIG. 5C), with a more gradual increase of low intensity seen in the other three. For the group given recombinant HBsAg, a second vaccination resulted in an increase in the HBsAg antibody titre in both animals, but the intensity of this increase was low, with animal SE in particular showing a very poor HBsAg antibody titre compared to that observed with the other animal in this group (rabbit F), or when compared to the group vaccinated with λ-HBsAg. This inconsistency of response has been previously reported for HBsAg (Alper, C. A., Kruskall, M. S., Marcus-Bagley, D., Craven, D. E., Katz, A. J., Brink, S. J., Dienstag, J. L., Awdeh, Z., and Yunis, E. J. Genetic prediction of nonresponse to hepatitis B vaccine N. Engl. J. Med. 1989; 321: 708-712).

End point titrations of HBsAg antibody responses were between 1:120-1:640 after 22 weeks for λ-HBsAg vaccinated rabbits (the titres were 1:10 at week 0), while titres of (Rabbit E) AND 1:600 (Rabbit F) were observed at the same time point for these rabbits (which were given recombinant λ-HBsAg). A high antibody response against λ phage coat proteins was observed in all rabbits vaccinated with λ-HBsAg following the first vaccination, suggesting that this high anti-phage response did not inhibit the efficiency of subsequent phage vaccinations (FIG. 5A-D). Anti-phage responses at week 22 had an end-point titration in the order of 1:50,000 for all 4 animals).

The invention claimed is:

1. An immunogenic formulation comprising a bacteriophage particle the surface of which is unmodified and a pharmaceutically acceptable carrier therefor, the bacteriophage particle comprising a eukaryotic promoter and an exogenous nucleic acid under control of the eukaryotic promoter and encoding a hepatitis virus type A and/or type B polypeptide which is capable of expression and presentation on the surface of an antigen presenting cell of an organism, such that an immune response to said polypeptide is raised in the organism.

2. The immunogenic formulation according to claim 1, wherein the hepatitis virus type A and/or type B polypeptide expressed and presented on the surface of the polypeptide presenting cell is a hepatitis surface antigen.

3. The immunogenic formulation hepatitis according to claim 1, wherein the bacteriophage has been engineered to express more than one hepatitis virus type A and/or type B polypeptide.

4. The immunogenic formulation according to claim 1, wherein the formulation comprises greater than $10^9$ bacteriophage particles.

5. The immunogenic formulation according to claim 1, which is capable of eliciting a humoral and/or cellular immune response.

6. The immunogenic formulation according to claim 1, wherein the bacteriophage comprises transcriptional and/or translational regulators to facilitate expression of the polypeptide in addition to the eukaryotic promoter.

7. The immunogenic formulation according to claim 1, wherein the eukaryotic promoter is selected from the group consisting of a CMV, SV40, thymidine kinase and RSV promoter.

8. The immunogenic formulation according to claim 1, wherein the exogenous nucleic acid is under the control of a constitutive promoter and a controllable promoter.

9. The immunogenic formulation according to claim 1, wherein the bacteriophage is lambda (λ), p1 phage, T phage, Mu, fd, M13 or a filamentous phage.

10. The immunogenic formulation according to claim 1, wherein the bacteriophage comprises one or more than one copy of a nucleotide sequence encoding the hepatitis virus type A and/or type B polypeptide.

11. The immunogenic formulation according to claim 1, wherein the bacteriophage is abortive to lytic growth in the natural bacterial flora of the chosen mammalian host.

12. The immunogenic formulation according to claim 1, further comprising inhibitors of lysosmal/endosomal enzymic catabolism and/or nuclear localisation signals.

13. The immunogenic formulation according to claim 1, further comprising an amount of the polypeptide to be expressed by the bacteriophage.

14. The immunogenic formulation according to claim 1, wherein the exogenous nucleic acid also encodes a polypeptide capable of augmenting the immune response.

15. The immunogenic formulation according to claim 1, further comprising an adjuvant.

16. The immunogenic formulation according to claim 1, wherein the bacteriophage is associated with a vehicle.

17. A method of raising an immune response comprising administering to a human or animal an effective amount of the formulation of claim 1.

* * * * *

UNITED STATES PATENT AND TRADEMARK OFFICE
CERTIFICATE OF CORRECTION

| | |
|---|---|
| PATENT NO. | : 7,910,110 B2 |
| APPLICATION NO. | : 10/529917 |
| DATED | : March 22, 2011 |
| INVENTOR(S) | : March et al. |

It is certified that error appears in the above-identified patent and that said Letters Patent is hereby corrected as shown below:

Column 13, Claim 3, Line 41: Please correct "formulation hepatitis according"
to read -- formulation according --

Signed and Sealed this
Twenty-fifth Day of October, 2011

David J. Kappos
*Director of the United States Patent and Trademark Office*